(12) United States Patent
Koste et al.

(10) Patent No.: US 7,615,009 B2
(45) Date of Patent: *Nov. 10, 2009

(54) SYSTEM AND METHOD FOR OPTICAL DATA TRANSMISSION IN ULTRASOUND IMAGING

(75) Inventors: Glen P. Koste, Niskayuna, NY (US); Samhita Dasgupta, Niskayuna, NY (US); Matthew Christian Nielsen, Scotia, NY (US); Min-Yi Shih, Carson City, NV (US); Robert John Filkins, Niskayuna, NY (US); Todd Ryan Tolliver, Clifton Park, NY (US); Bruno Hans Haider, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 93 days.

This patent is subject to a terminal disclaimer.

(21) Appl. No.: 11/678,038

(22) Filed: Feb. 22, 2007

(65) Prior Publication Data

US 2007/0167816 A1 Jul. 19, 2007

Related U.S. Application Data

(63) Continuation-in-part of application No. 10/812,243, filed on Mar. 29, 2004, now Pat. No. 7,367,945.

(51) Int. Cl.
*A61B 8/00* (2006.01)
(52) U.S. Cl. .................................................. 600/443
(58) Field of Classification Search .................. 600/437, 600/459, 443
See application file for complete search history.

(56) References Cited

U.S. PATENT DOCUMENTS

| | | | |
|---|---|---|---|
| 571,823 A | 11/1896 | Briggs | |
| 4,739,521 A | 4/1988 | Akimoto | |
| 4,923,288 A | 5/1990 | Allen et al. | |
| 5,010,346 A | 4/1991 | Hamilton et al. | |
| 5,081,993 A | 1/1992 | Kitney et al. | |
| 5,353,262 A * | 10/1994 | Yakymyshyn et al. | 367/149 |
| 5,396,362 A | 3/1995 | Yakymyshyn et al. | |
| 5,419,329 A | 5/1995 | Smith et al. | |
| 5,422,904 A * | 6/1995 | Gorfinkel et al. | 372/50.1 |

(Continued)

FOREIGN PATENT DOCUMENTS

EP 0762142 A1 3/1997

(Continued)

OTHER PUBLICATIONS

U.S. Appl. No. 10/436,929, filed May 12, 2003, entitled "Crosslinked Polymers" by James A. Cella, et al.

(Continued)

*Primary Examiner*—Eric F Winakur
(74) *Attorney, Agent, or Firm*—Ann M. Agosti

(57) ABSTRACT

A system and method for optical transmission of ultrasound data signals from a probe to an image processing system is provided. By using a silicon-based optical modulator to encode ultrasound data signals onto an optical signal, an optical transmission link between the ultrasound probe and the image processing system can achieve a high signal to noise ratio with a lower power input.

13 Claims, 8 Drawing Sheets

U.S. PATENT DOCUMENTS

| | | | |
|---|---|---|---|
| 5,532,981 | A | 7/1996 | Duggal et al. |
| 5,565,867 | A | 10/1996 | Tiemann |
| 5,566,133 | A | 10/1996 | Engeler et al. |
| 5,715,823 | A | 2/1998 | Wood et al. |
| 5,718,226 | A | 2/1998 | Riza |
| 5,739,936 | A | 4/1998 | Yakymyshyn et al. |
| 5,949,491 | A | 9/1999 | Callahan et al. |
| 6,101,407 | A | 8/2000 | Groezinger |
| 6,118,397 | A | 9/2000 | Heflinger |
| 6,139,497 | A | 10/2000 | Amemiya et al. |
| 6,142,946 | A | 11/2000 | Hwang et al. |
| 6,248,069 | B1 | 6/2001 | Liu et al. |
| 6,476,541 | B1 * | 11/2002 | Smith et al. ............... 310/334 |
| 6,529,150 | B1 | 3/2003 | Shoop et al. |
| 6,569,097 | B1 | 5/2003 | McMorrow et al. |
| 6,609,425 | B2 | 8/2003 | Ogawa |
| 6,783,494 | B2 | 8/2004 | Ogawa |
| 6,890,301 | B2 | 5/2005 | Jago et al. |
| 2005/0111777 | A1 * | 5/2005 | Stenger et al. ............... 385/14 |

FOREIGN PATENT DOCUMENTS

| | | |
|---|---|---|
| EP | 0763192 B1 | 7/2000 |

OTHER PUBLICATIONS

U.S. Appl. No. 10/437,278, filed May 12, 2003, entitled "Thermally Crosslinked Polymers" by James A. Cella, et al.

A. Huang et al., "13.7 A 10Gb/s Photonic Modulator and WDM MUX/DEMUX Integrated with Electronics in 0.13um SOI CMOS," 2006 IEEE International Solid-State Circuits Conference, pp. 24-25.

"Fiber Will Displace Copper Sooner Than You Think," 2005 Luxtera, pp. 1-19.

* cited by examiner

SYSTEM AND METHOD FOR OPTICAL DATA TRANSMISSION IN ULTRASOUND IMAGING

CROSS REFERENCE TO RELATED APPLICATIONS

The present application is a continuation-in-part of and claims the benefit of U.S. Ser. No. 10/812,243, filed on Mar. 29, 2004, the disclosure of which is incorporated herein by reference.

BACKGROUND OF THE INVENTION

The invention relates generally to ultrasound systems, and more specifically to a method and system for design of an ultrasound probe utilizing optical transmission for communicating ultrasound signals to an image processing station or system.

Conventional ultrasound scanners comprise an ultrasound probe for transmitting ultrasound signals to an area to be examined as well as for receiving scattered waves. The ultrasound probe usually comprises several transducer elements that are configured for sensing the backscattered waves. The transducer elements convert the backscattered waves to corresponding electrical signals. The electrical signals are transmitted to a processing unit where the electrical signals are processed to generate a corresponding image of the area that was scanned.

Typically, the electrical signals are transferred to the processing unit by cables. While designing the ultra-sound probe, it is desirable to maintain the diameter of the probe cable at a size that is maneuverable by an operator. In addition, it is often desirable to obtain a high resolution for the image generated by the ultrasound system. One way to increase the resolution is to increase the number of transducer elements in the ultrasound probe. One problem with increasing the number of transducer elements is the increase in the cable diameter. An increase in the cable diameter results in restrictive maneuverability of the ultrasound probe. Moreover, in an effort to maintain signal integrity, the length of the cable is sometimes limited to a short distance. Thus, the mobility of the ultrasound scanner is restricted to a large extent.

In addition, the transducer elements generate substantial amounts of heat when operating. The heat generated may cause inconvenience to an operator who is using the ultrasound probe and can lend to other temperature issues of the probe hardware.

It is therefore desirable to increase sensitivity of the ultrasound probe while maintaining the diameter of the probe and also maintain the probe temperature at a desired level. It is also desirable to increase the length of the probe cable to provide better mobility.

BRIEF DESCRIPTION OF THE INVENTION

The present invention provides a system and method for ultrasound imaging in which ultrasound scan data is communicated between a probe head and an image processing station via optical transmission. Embodiments of the present invention may utilize an optical modulator which operates by using silicon-based semiconductors, such as CMOS optical modulators.

In accordance with one aspect of the invention, an ultrasound system is provided, having an ultrasound probe with a number of transducers and an image processor which receives scan signals from the transducers to process an image therefrom. The ultrasound system also includes an optical transmission link connected between the probe and the image processing system. The optical transmission link is configured to communication the scan signals and has at least one silicon-based optical modulator.

According to another aspect of the invention, a method for ultrasound imaging includes acquiring ultrasound data from an object of interest and electrically communication the data to an optical modulator. The method also includes forward biasing the optical modulator and modulating an optical signal in accordance with the ultrasound data. The modulated optical signal is then transmitted to an imaging subsystem for image reconstruction.

In accordance with a further aspect of the invention, an ultrasound probe having an array of transducers and a receiver to acquire ultrasound scan data from the transducers is provided. The probe further includes a light source input connected to receive a light signal and an optical modulator connected to the receiver and configured to modulate the light signal to encode the ultrasound scan data thereon. The optical modulator includes a number of semiconductors.

Various other features and advantages of the present invention will be made apparent from the following detailed description and the drawings.

BRIEF DESCRIPTION OF THE DRAWINGS

The drawings illustrate one embodiment presently contemplated for carrying out the invention.

In the drawings.

DETAILED DESCRIPTION OF THE PREFERRED EMBODIMENT

A system is shown to provide for optical transmission of ultrasound signals between an ultrasound probe and an image processing unit or system.

Figure 1:
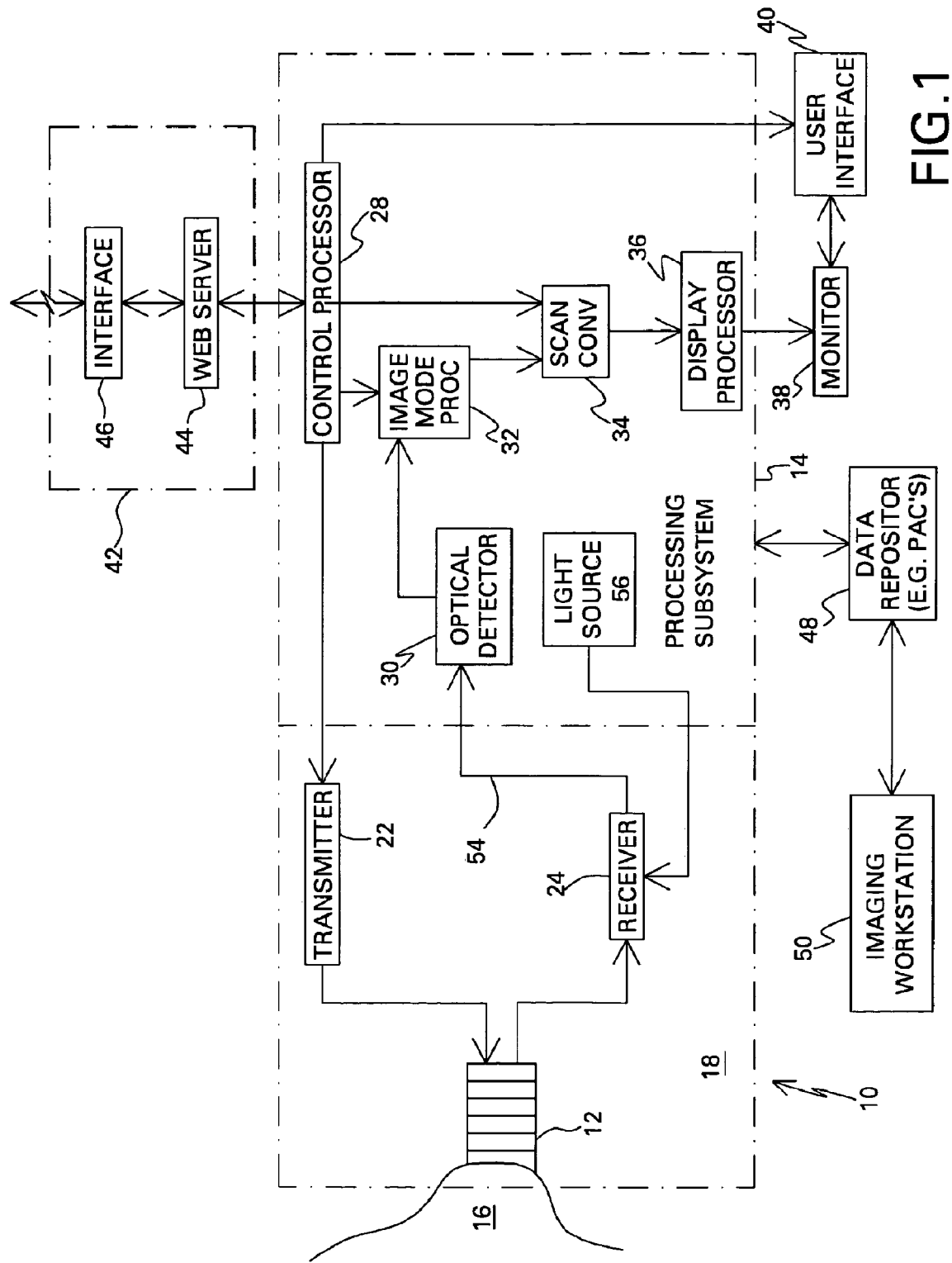
FIG. 1 is a block diagram illustrating an exemplary ultrasound system implemented according to one aspect of the invention.
Figure 2:
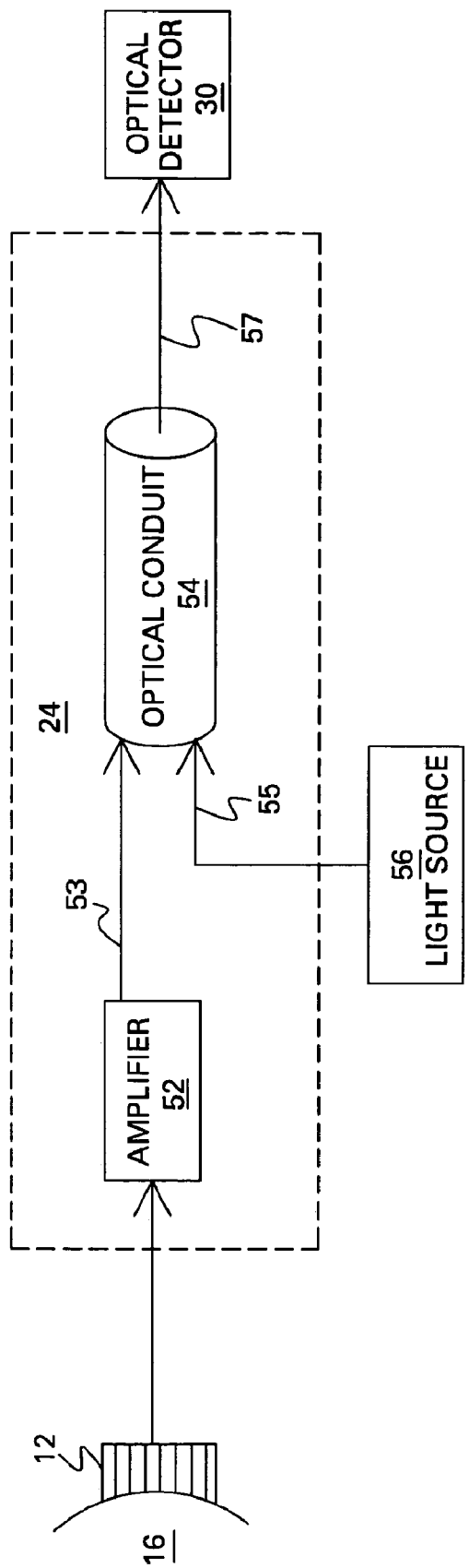
FIG. 2 is a block diagram of one embodiment of an acquisition subsystem implemented according to one aspect of the invention.

In one embodiment of the present invention, an ultrasound system 10 for generating an image is provided as shown in FIG. 1. The ultrasound system generally comprises an ultrasound probe 18 configured for sensing ultrasound signals and transmitting electrical signals representative of the sensed ultrasound signals. The ultrasound probe comprises transducer array 12, transmitter 22, and receiver 24. The electrical signals are transmitted to optical detector 30 via optical conduit 54. The optical conduit 54, as shown in FIG. 2, is configured for coupling a light source 56 and an optical detector 30 in an optical path. The optical conduit 54 comprises electro-optic modulators configured for modulating optical signals on the optical conduit with at least one of the ultrasound signals to generate corresponding optically modulated analog signals on the optical conduit. The optical conduit will be further described in detail with reference to FIG. 2. The ultrasound probe will be further described in detail with reference to FIG. 4.

In one more specific aspect of the present invention, the ultrasound signals transmitted by the ultrasound probe comprise analog electrical signals. In another more specific aspect of the present invention, which may be used in combination or separately from the analog electrical signal aspect, the electro-optic modulators comprise electro-optic polymer modulators. This aspect is advantageous because electro-optic polymer devices are compact and flexible, and can be densely packed to fit a head of a probe. In addition, electro-optic polymer devices consume lower power.

Referring now to FIG. 1, a block diagram of an illustrative, more specific embodiment of an ultrasound system 10 implemented in accordance with one aspect of the invention is shown. The ultrasound system comprises an ultrasound probe 12 a transmitter 22 and a receiver 24. The ultrasound system further comprises a processing subsystem 14 comprising a control processor 28, an optical detector 30, an imaging mode processor 32, a scan converter 34 and a display processor 36. The display processor is further coupled to a monitor 38 for displaying images. User interface 40 interacts with the control processor 28 and the display monitor 38. The control processor 28 may also be coupled to a remote connectivity subsystem 42 comprising a web server 44 and a remote connectivity interface 46. Processing sub-system 14 may be further coupled to data repository 48 to receive ultrasound image data. The data repository 48 interacts with an imaging workstation 50.

The aforementioned architectures and modules may be dedicated hardware elements, such as circuit boards with digital signal processors, or may be software running on a general purpose computer or processor, such as a commercial, off-the-shelf PC. The various architectures and modules may be combined or separated according to various embodiments of the invention.

As illustrated in FIG. 1, the ultrasound probe 12 is in contact with subject 16. The ultrasound probe 12 is coupled to the output of transmitter 22 and the input of receiver 24. In processing subsystem 14, the output of optical detector 30 is coupled to an input of imaging mode processor 32. Control processor interfaces to imaging mode processor 32, scan converter 34 and to display processor 36. An output of imaging mode processor 32 is coupled to an input of scan converter 34. An output of scan converter 34 is coupled to an input of display processor 36. The output of display processor 36 is coupled to monitor 38.

Ultrasound system 10 transmits ultrasound energy into subject 16 and receives and processes backscattered ultrasound signals from the subject to create and display an image. To generate a transmitted beam of ultrasound energy, the control processor 28 sends command data to the transmitter 22 to generate transmit parameters to create a beam of a desired shape originating from a certain point at the surface of the ultrasound probe 12 at a desired steering angle.

The transmitter 22 uses the transmit parameters to properly encode transmit signals to be sent to the ultrasound probe 12. The transmit signals are set at certain levels and phases with respect to each other and are provided to individual transducer elements of the ultrasound probe 12. The transmit signals excite the transducer elements to emit ultrasound waves with the same phase and level relation-ships. As a result, a transmitted beam of ultrasound energy is formed in a subject within a scan plane along a scan line when the ultrasound probe 12 is acoustically coupled to the subject by using, for example, ultrasound gel. The process is known as electronic scanning.

The ultrasound probe 12 is a two-way transducer. When ultrasound waves are transmitted into a subject, the ultrasound waves are backscattered off the tissue and blood samples within the structure. The ultrasound probe 12 receives the backscattered waves at different times, depending on the distance into the tissue they return from and the angle with respect to the surface of the ultrasound probe 12 at which they return. In one embodiment, the transducer elements are configured for sensing the backscattered waves and converting the ultrasound signals to corresponding analog electrical signals.

The received electrical signals are routed through receiver 24 to the processing subsystem 14. Optical detector 30 converts the optically modulated analog signals received from receiver 24 to electrical signals. The electrical signals are transferred to imaging mode processor 32. Imaging mode processor 32 uses parameter estimation techniques to generate imaging parameter values from the demodulated data in scan sequence format. The imaging parameters may comprise parameters corresponding to various possible imaging modes such as, for example, B-mode, color velocity mode, spectral Doppler mode, and tissue velocity imaging mode. The imaging parameter values are passed to scan converter 34. Scan converter 34 processes the parameter data by performing a translation from scan sequence format to display format. The translation includes performing interpolation operations on the parameter data to create display pixel data in the display format.

The scan converted pixel data is sent to display processor 36 to perform any final spatial or temporal filtering of the scan converted pixel data, to apply grayscale or color to the scan converted pixel data, and to convert the digital pixel data to analog data for display on monitor 38. The user interface 40 interacts with the control processor 28 based on the data displayed on monitor 38.

FIG. 2 is a block diagram of an embodiment of receiver 24 implemented according to one aspect of the invention. As described above, the received electrical signals are routed through receiver 24 to the processing subsystem 14. Receiver 24 comprises amplifier 52, light source 56, and optical detector 30. The light source is coupled to the optical detector via an optical conduit 54. Each component of the receiver is described in further detail below.

Amplifier 52 is configured for amplifying the received analog electrical signals from the ultrasound probe 12. In one embodiment, the received electrical signals range from micro-volts to milli-volts and may be amplified to a few volts. In one embodiment, the amplifier is implemented using analog devices such as transistors. Optical conduit 54 receives the amplified analog electrical signals from amplifier 52 on line 53. The optical conduit also receives continuous wave light generated by light source 56 on line 55. The optical conduit is configured for transforming the analog electrical signals into optically modulated analog signals, which are transmitted to the optical detector 30 on line 57. Transmitting the optically modulated analog signals is advantageous in that it eliminates the need for an analog to digital converter in the probe. The presence of the analog to digital converter in typical probe systems results in higher power requirements. In addition, the probe size is increased due to the addition of the analog to digital converter.

Optical detector 30 is configured to convert the optically modulated analog signals to corresponding electrical signals. The electrical signals are then transmitted to the processing subsystem for further signal processing. In one embodiment, the optical conduit comprises a fiber optic cable. In a further embodiment, the fiber optic cable comprises an optical waveguide and a plurality of optical fibers. As described above, the optical conduit is configured for transforming the electric signals to optical signals. The transformation is accomplished by using electro-optic modulators as illustrated in FIG. 3.

Figure 3:
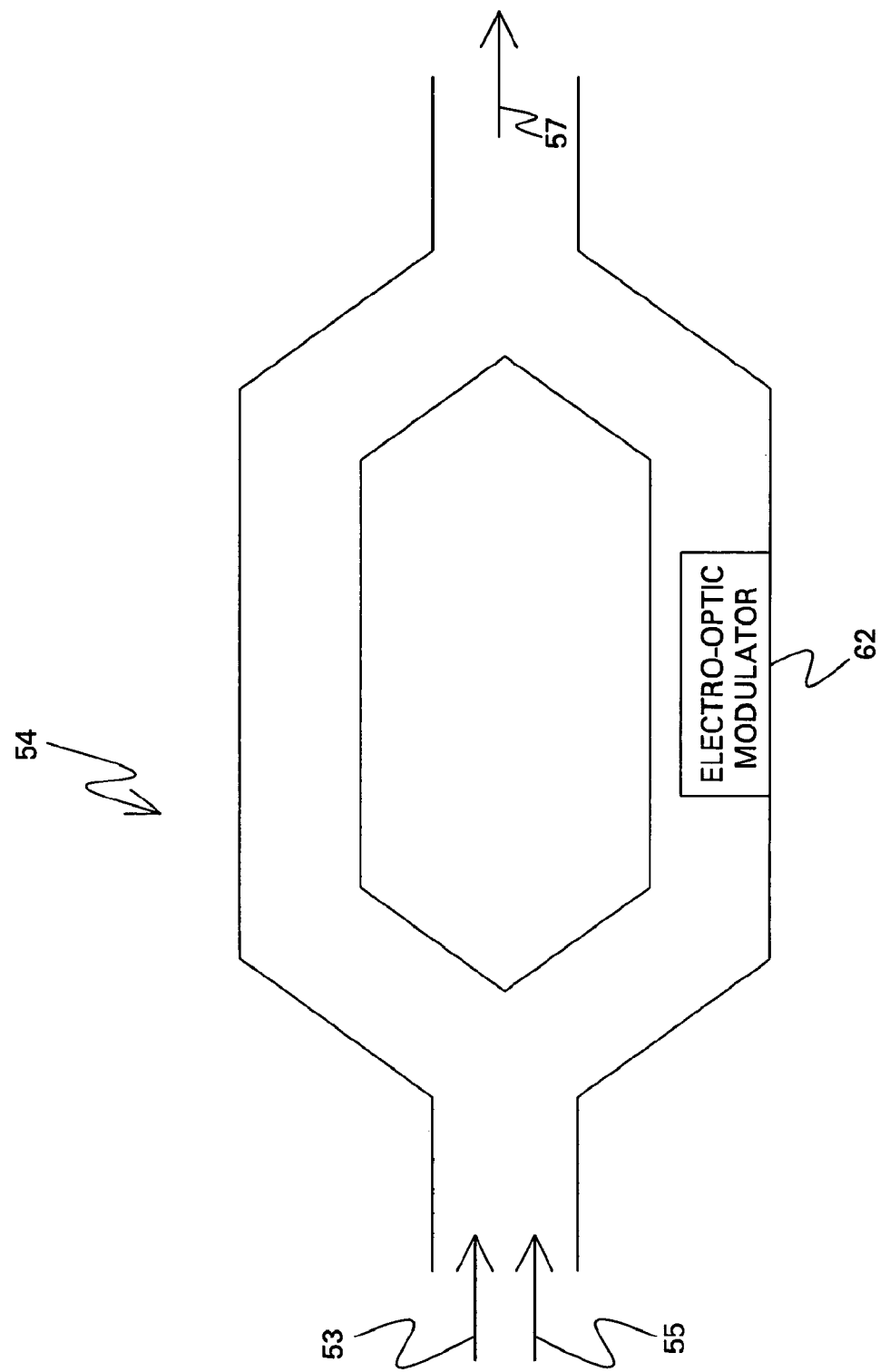
FIG. 3 is a block diagram of one embodiment of a modulator implemented according to one aspect of the invention.
Figure 4:
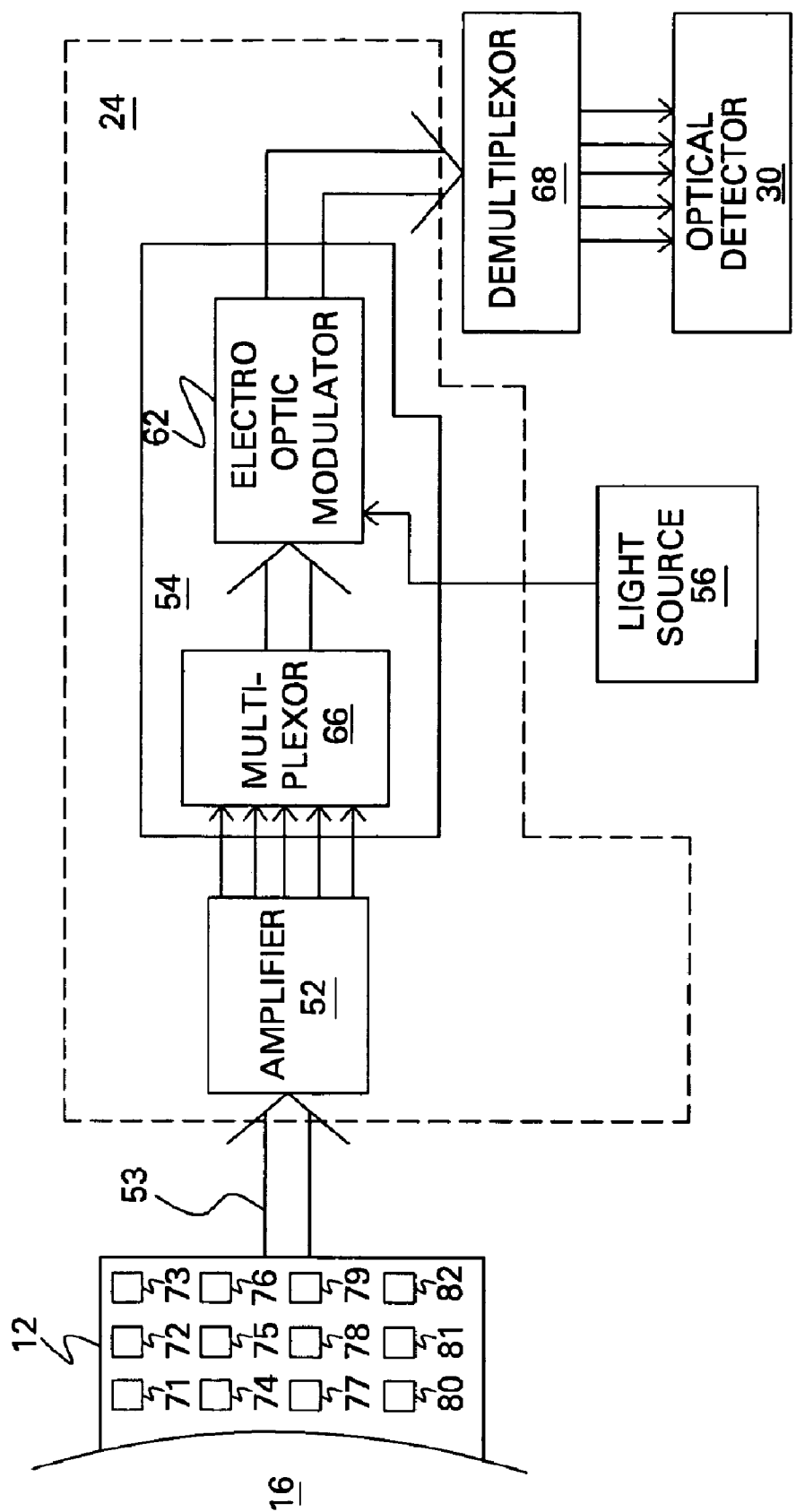
FIG. 4 is a block diagram of an embodiment of a receiver implemented according to one aspect of the invention.

FIG. 3 is a block diagram illustrating an optical waveguide using an electro-optic modulator implemented according to one aspect of the invention. Optical waveguide 54 receives the electrical signals from the ultrasound probe 12 as well as continuous wave light from light source 56 as inputs. Electro-optic modulator 62 is configured for modulating the continuous wave light with the electrical signals received from the ultrasound probe to generate the optically modulated analog signals shown by reference numeral 57. The optically modulated analog signals are then transmitted to optical detector 30 and the processing subsystem 14 for further processing. The electro-optic modulator 62 is implemented using polymer materials. Polymer materials are well-suited for use in electro-optic modulators because of their compactness and reduced input power requirements. In addition, polymer modulators are lossless devices, and hence do not generate a substantial amount of heat in the ultrasound system. In a further embodiment of the invention as illustrated in FIG. 4, a multiplexer 66 is used in receiver 24. As described with reference to FIG. 1, ultrasound probe 12 comprises a plurality of transducer elements 71-82, each transducer configured to generate an electrical signal representative of the backscattered waves. The electrical signals are collectively shown by reference numeral 53.

Multiplexer 66 of FIG. 4 is configured for coupling the electro-optic modulator 62 and a corresponding set of transducers and conducting the electrical signals from the set of transducers to the electro-optic modulator. For example, in one embodiment, multiplexer 66 couples transducers 71-76 to electro-optic modulator 62. In a further embodiment, multiplexer 66 includes a plurality of multiplexers and optical conduit 54 includes a plurality of electro-optic modulators. In such an arrangement, the multiplexers are configured to couple a set of transducers and a corresponding set of electro-optic modulators. In addition, optical signals can be multiplexed by using wavelength, allowing many electrical signals to be transmitted on a single optical fiber, which typically results in better image resolution without having to increase cable requirements.

Demultiplexer 68 is configured for demultiplexing the optically modulated analog signals received from the electro-optic modulators. The de-multiplexed optically modulated analog signals are transmitted to optical detector 30. Optical detector 30 comprises a plurality of photosensitive devices. Each demultiplexed optically modulated analog signal generated by the de-multiplexer is coupled to a respective photosensitive device in the optical detector. The photosensitive devices in turn are configured to convert the optically modulated analog signals to electrical signals. In a further embodiment, de-multiplexer 68 comprises a plurality of demultiplexers and optical conduit 54 comprises a plurality of electro-optic modulators.

Figure 5:
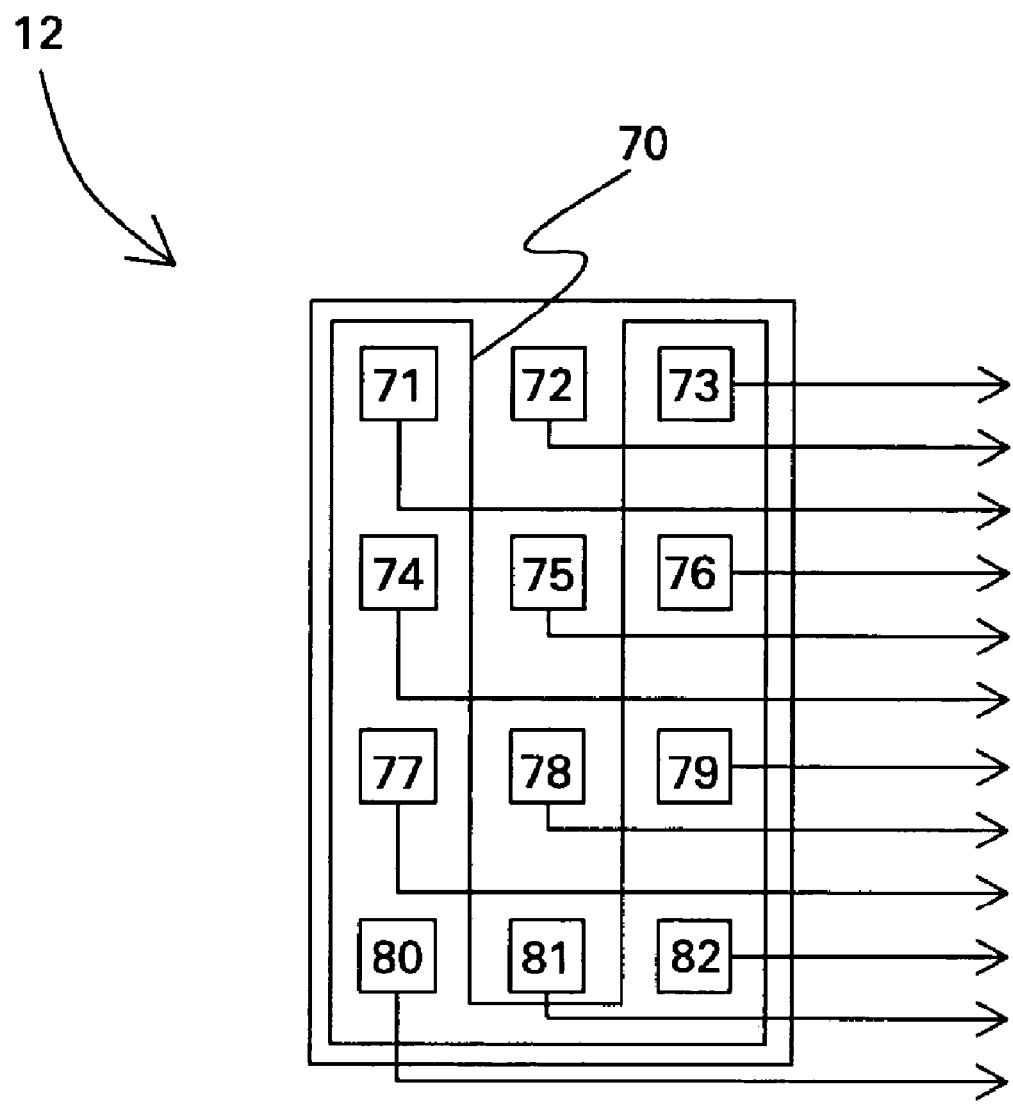
FIG. 5 is a block diagram of an ultrasound probe implemented according to one aspect of the invention.

In a further embodiment, illustrated in FIG. 5, the ultrasound probe 12 of the ultrasound system further comprises cooling line 70 configured for maintaining a probe temperature. In an alternate embodiment, the ultrasound probe comprises a plurality of cooling lines configured for maintaining a probe temperature.

The ultrasound probe illustrated in FIG. 5 comprises transducer elements 71-82. The ultrasound probe additionally comprises electronic and optical components 24 as shown in FIG. 4. The cooling line 70 is configured for absorbing the heat generated by the transducer elements and electronic components. In one embodiment, the cooling line comprises a coolant. Examples of the coolant used include water, water/alcohol mixtures, perfluorinated liquids, and combinations thereof. The cooling fluid absorbs heat from the probe through a heat exchanger. The heated fluid is returned back to the system where the heat is removed from the fluid by means of a second heat exchanger. The subsequently cooled fluid is pumped back to the probe where this process cycle repeats.

Figure 6:
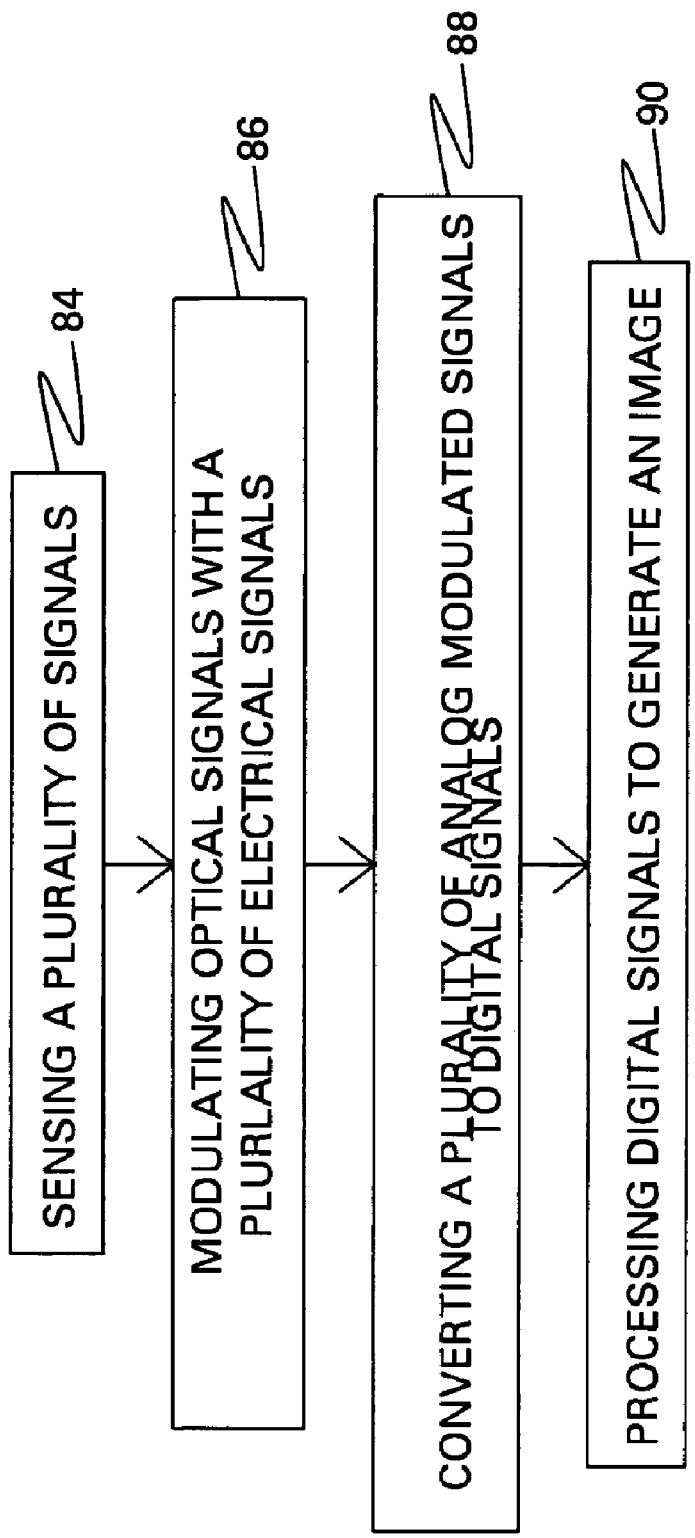
FIG. 6 is a flow chart illustrating one method by which the invention is implemented.

The above described invention is illustrated as steps in a flow chart. FIG. 6 is a flow chart illustrating the various steps in the invention. Each step is described in further detail below.

In step 84, a plurality of signals is sensed and corresponding electrical signals are generated. In one embodiment, the plurality of signals comprises ultrasound signals. The ultrasound signals are sensed using an ultra-sound probe. In one embodiment, the ultrasound probe comprises piezoelectric transducers.

In step 86, the electrical signals are modulated with a plurality of optical signals to generate a corresponding plurality of optically modulated analog signals. In one embodiment, the electrical signals are modulated using electro-optic modulators. In a more specific embodiment, the electro-optic modulators comprise polymer electro-optic modulators. In a further specific embodiment, the electro-optic modulator comprises Mach Zehnder electro-optic modulators.

In step 88, the plurality of optically modulated analog signals is converted to a corresponding plurality of digital signals. In step 90, the plurality of digital signals is processed to generate the image.

Figure 7:
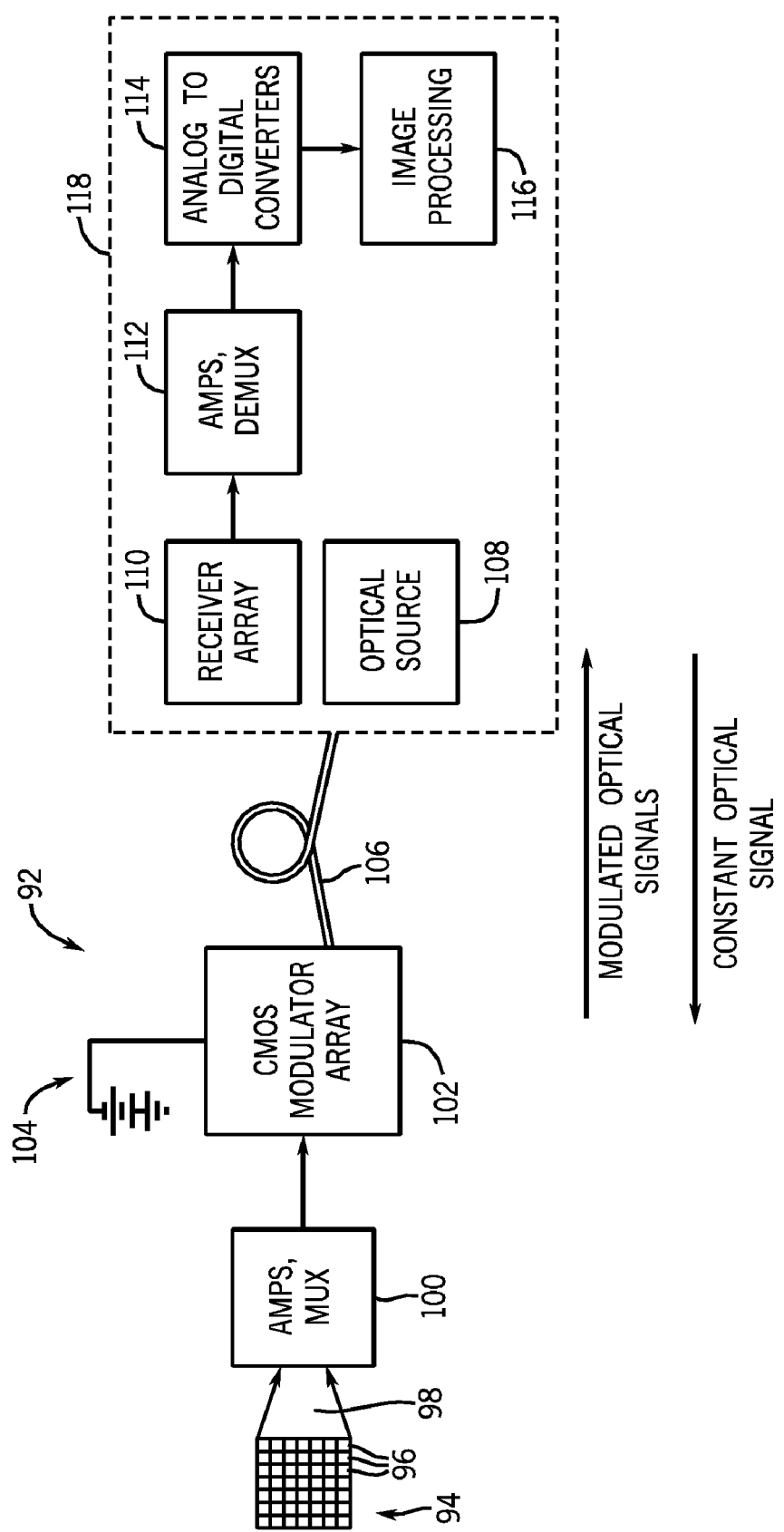
FIG. 7 is a block diagram of an exemplary ultrasound system implemented according to a further aspect of the invention.

Referring now to FIG. 7, another embodiment of the present invention is shown in which optical modulation is achieved via a silicon-based optical modulator. Such an optical modulator may be used in place of or in combination with the modulators discussed above. Ultrasound system 92 of FIG. 7 includes an ultrasound probe head 94 which has a plurality of transducers 96. As known in the art, the number and type of transducers as well as the sensitivity or resolution of the probe may vary. Thus, it is appreciated that one or several channels of electrical scan signals 98, representing ultrasound data, from the probe head may be amplified and multiplexed by a low-noise amplifier and multiplexer circuit 100. Preferably, the amplification components of circuit 100 are configured for low noise applications, to preserve signal-to-noise ratio (SNR). In alternate embodiments, the ultrasound data signals 98 from probe head 94 may be conditioned by other circuits, such as impedance-matching gain circuits (not shown). Additionally, it is understood that amplification, multiplexing, and/or modulation may take place on a common chip or circuit board integrated into the probe head 94.

Optical modulator array 102, in combination with optical fiber 106, optical source 108 and receiver array 110 create an optical transmission link between probe 94 and an imaging system 118. Optical modulator array 102 receives the output of amplification and multiplexing circuit 100 and modulates an optical signal, such as a constant laser or other light energy. By modulating the optical signal in accordance with the one or more channels of ultrasound data signals 98 of the probe head 94, optical modulator array 102 can encode the data signals 98 onto the optical signal. Thus, optical modulator array 102 may include one or many optical modulators, which may or may not correspond to the number of channels of ultrasound data signals 98 of probe 94. Optical source 108 generates the optical signal used by optical modulator array 102 and transmits the optical signal to the modulator array 102 via a fiber optic cable 106. Preferably, optical modulator array 102 is an array of silicon-based optical modulators which utilize semiconductive elements to modulate an optical signal and can be manufactured using CMOS processes. Therefore, optical source 108 may be a single-mode or constant output laser and may be designed for lower power operation than the optical sources commonly used for optical transmission without CMOS modulators.

As the optical signal from the optical source 108 passes through the CMOS modulator array 102, it is split, phase shifted, and recombined to produce a modulated output. The functions of CMOS modulator array 102 (splitting, phase shifting, recombining, as well as optical signal wave guiding, and optical signal transport) may be carried out through the use of PIN-diode based waveguides and are preferably performed all on a single microchip. A preferred CMOS optical modulator known as the CMOS Photonics™ Platform is available from Luxtera, Inc., 1819 Aston Ave., Suite 102, Carlsbad, Calif. 92008. In addition, modulator array 102 may be controlled by a bias circuit 104, representationally shown as a DC voltage. Bias circuit 104 is designed to apply a biasing voltage of a desired amount to maintain modulator 102 in a forward bias mode.

The modulated optical output by modulator array 102 is transmitted across an optical fiber 106 to an imaging system 118 for processing and image reconstruction. Optical fiber 106 may include multiple optical conduits for simultaneous transmission of more than one channel of ultrasound data. Imaging system 118 contains an optical-to-electric converter or receiver 112 which produces an electrical output equivalent to the modulated optical carrier. Receiver 110 may therefore include one or more photodiodes or other optical detection devices. The electrical signals output by the receiver 110 are then filtered and conditioned by an amplifying and multiplexing circuit 114. Additionally, imaging system 118 may also contain impedance matching circuits, mixers, various filters, or other pre-processing and conditioning components (not shown). An analog-to-digital converter 114 digitizes the electrical signals of the receiver 110 for processing, storage, and/or image reconstruction by image processing unit 116. By utilizing the optical data transmission of FIG. 7, ultrasound systems can achieve lower noise data transfer, with less susceptibility to EMI, and requiring lower optical power for longer transmission.

Figure 8:
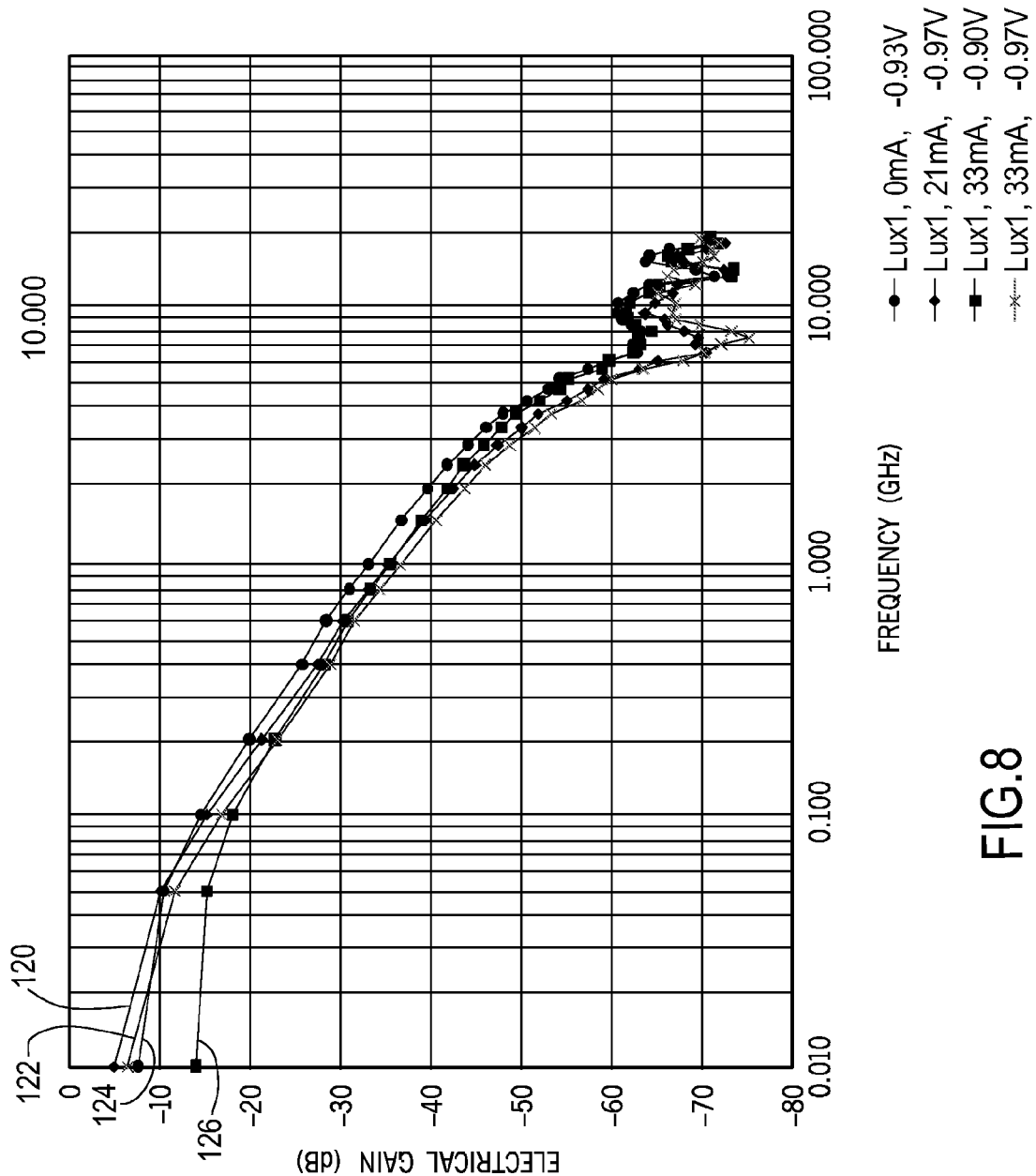
FIG. 8 is a graph of gain versus bandwidth for an optical modulator operating in accordance with an embodiment of the invention.

As mentioned above, optical modulators used in accordance with the present invention may be based on PIN diode waveguides set to operate in a forward-bias mode of operation. Typically, optical modulators such as the CMOS Photonics™ Platform are used for mass digital data transfer (such as in network communication) in which a higher bandwidth is desirable. Thus, these modulators are operated in a reverse-bias mode which can achieve a higher bandwidth (10 GHz and above) at the cost of a higher noise component. However, as known in the art, ultrasound data transfer often occurs at only significantly lower bandwidths and is optimized when the noise component is low (about 3 dB). FIG. 8 is a graph of the performance of an exemplary optical modulator operating in a forward-bias mode. Each data plot line 120-126 represents the measured signal gain versus frequency for a number of biasing currents and voltages. At relatively low frequencies, such as 20 MHz, all four plot lines 172-178 exhibit a high signal gain. However, signal gain drops precipitously as bandwidth approaches 10 GHz. Thus, a forward bias is beneficial for use in transmitting ultrasound signals, but may not be as beneficial for transmitting large amounts of data at higher bandwidths. In addition, the bias voltage applied to an optical modulator can affect the gain-bandwidth curve. As shown, a 33 mA, −0.90V bias voltage 126 will have a lower initial gain versus a 21 mA, −0.97V bias voltage. Therefore, it is appreciated that embodiments of the present invention may be adaptable to meet varying gain and bandwidth characteristics in a forward bias mode.

The previously described embodiments of the present invention have many advantages, including providing a light ultrasound probe by using optical fibers which provides easier maneuverability. In addition, the temperature of the ultrasound probe may also be maintained by incorporating a cooling line in the design. A technical contribution for the disclosed method and apparatus is that it provides for a semiconductor-implemented modulation technique for optical data transmission between an ultrasound probe and the corresponding image processing system.

Therefore, one embodiment of the present invention includes an ultrasound system having a probe, an image processor, and an optical transmission link. The image processor is configured to receive scan signals of a number of transducers of the probe, and to process an image based on these signals. The optical transmission link is connected between the probe and the image processing system and has at least one silicon-based optical modulator. The link is configured to communicate the scan signals between the probe and the image processing system.

According to another embodiment of the invention, a method for ultrasound imaging is disclosed. The method includes acquiring ultrasound data from an object of interest and electrically communication the data to an optical modulator. The method also includes forward biasing the optical modulator and modulating an optical signal in accordance with the ultrasound data. The modulated optical signal is then transmitted to an imaging subsystem for image reconstruction.

In accordance with a further embodiment of the invention, an ultrasound probe is provided. The probe includes a transducer array having a plurality of transducers and a receiver configured to acquire ultrasound scan data from the transducers. A light source input of the probe is connected to receive a light signal. The light signal is modulated by an optical modulator connected to the receiver and configured to modulate the light signal to encode the ultrasound scan data thereon. The optical modulator includes a number of semiconductors.

The present invention has been described in terms of the preferred embodiment, and it is recognized that equivalents, alternatives, and modifications, aside from those expressly stated, are possible and within the scope of the appending claims.

What is claimed is:
1. An ultrasound system comprising:
   an ultrasound probe having a plurality of transducer elements for sensing ultrasound signals and converting the ultrasound signals to analog electrical signals;
   an optical transmission link having at least one silicon-based electro-optical modulator, wherein the optical transmission link receives the analog electrical signals from the ultrasonic probe and optical signals from a light source, and modulates the optical signals with the analog electrical signals;

a circuit configured to apply a biasing voltage to the at least one electro-optical modulator to maintain the at least one silicon-based electro-optical modulator in a forward-bias mode;

an optical detector for converting the plurality of optically modulated analog signals to a corresponding plurality of digital signals; and an imaging system electrically coupled to the optical detector and configured to process the plurality of digital signals to generate an ultrasound image.

2. The ultrasound system of claim 1 wherein the light source is at least one of a single-mode laser source and a low power laser source.

3. The ultrasound system of claim 1, wherein the at least one silicon-based electro-optical modulator comprises an array of semiconductive elements.

4. The ultrasound system of claim 1 wherein the at least one silicon-based electro-optical modulator is constructed to perform multiplexing, optical signal transport, and modulation within a microchip.

5. The ultrasound system of claim 1, wherein the at least one silicon-based electro-optical modulator comprises a complementary-metal-oxide-semiconductor (CMOS) modulator array.

6. A method for ultrasound imaging comprising:
sensing ultrasound signals;
convening the ultrasound signals to analog electrical signals;
receiving optical signals from a light source;
electrically communicating the optical signals to at least one silicon-based electro-optical modulator;
modulating the optical signals with the analog electrical signals while apply a biasing voltage to the at least one silicon-based electro-optical modulator to maintain the at least one silicon-based electro-optical modulator in a forward-bias mode;
converting the plurality of optically modulated analog signals to a corresponding plurality of digital signals; and
processing the plurality of digital signals to generate an ultrasound image.

7. The method of claim 6 further comprising conditioning electrical signals representing the analog electrical signals to improve a signal-to-noise ratio when transmitting the modulated optical signal to the imaging system.

8. The method of claim 6 wherein the silicon-based optical modulator comprises an array of semiconductive elements.

9. The method of claim 6 wherein said modulating step comprises multiplexing and transporting the number of optical signals on a silicon chip.

10. The method of claim 6 wherein the light source comprises a laser source.

11. An ultrasound system comprising:
an ultrasonic probe including a transducer array having a plurality of transducer elements configured for sensing ultrasound signals and converting the ultrasound signals to analog electrical signals;
a complementary-metal-oxide-semiconductor (CMOS) modulator array that receives the analog electrical signals from the ultrasonic probe and optical signals from a light source, the CMOS modulator array encoding the analog electrical signals from the ultrasonic probe onto the optical signals from the light source to produce modulated optical signals;
a biasing circuit configured to maintain the CMOS modulator array in a forward-bias mode;
an optical-to-electrical converter that receives the modulated optical signals from the CMOS modulator array and produces an equivalent electrical output;
an analog-to-digital converter for converting the electrical output from the optical-to-electrical converter to a plurality of digital signals; and
an image processing unit for processing the plurality of digital signals to generate an ultrasound image.

12. The ultrasound system of claim 11 further comprising at least one amplifier configured to amplify the electrical output from the optical-to-electrical converter to improve a signal-to-noise ratio of the modulated optical signals.

13. The ultrasound system of claim 11 wherein the light source is a single-mode or constant output laser.

* * * * *